(12) United States Patent
Levin et al.

(10) Patent No.: US 6,414,165 B1
(45) Date of Patent: Jul. 2, 2002

(54) PREPARATION OF CIS-6, 6-DIMETHYL-3-OXA-BICYCLO[3.1.0]HEXAN-2-ONE

(75) Inventors: Daniel Levin, Macclesfield; Jonathan Guy; Nicholas Greeves, both of Liverpool, all of (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/673,377

(22) PCT Filed: Apr. 19, 1999

(86) PCT No.: PCT/GB99/01190

§ 371 (c)(1),
(2), (4) Date: Oct. 16, 2000

(87) PCT Pub. No.: WO99/54324

PCT Pub. Date: Oct. 28, 1999

(30) Foreign Application Priority Data

Apr. 22, 1998 (GB) ................................. 9808619

(51) Int. Cl.⁷ ............................................. C07D 307/04
(52) U.S. Cl. ........................................................ 549/302
(58) Field of Search ........................................ 549/302

(56) References Cited

U.S. PATENT DOCUMENTS

| 3,723,649 A | 3/1973 | Pitegoff et al. ............... 178/7.1 |
| 3,728,372 A | 4/1973 | Siddall .................... 260/456 R |
| 4,014,918 A | 3/1977 | Martel ........................ 260/468 |
| 4,508,914 A | 4/1985 | Schmidt ..................... 549/323 |

FOREIGN PATENT DOCUMENTS

| DE | 1 935 320 | 1/1970 |
| EP | 0 003 666 A1 | 8/1979 |

OTHER PUBLICATIONS

Takano, Seiichi, et al., "General Chirate Route to Irregular Monoterpenes via a Common Intermediate: Synthesis of (S)–Lavandulol, cis–(1S,3R)–Chrysanthemol, (1S,2R)–Rothrockene, and (R)–Santolinatriene", J. Org. Chem., 50, 931–936 (1985).

Green, Graham, et al., "Oxo Complexes of Ruthenium(VI) and (VII) as Organic Oxidants", J.Chem, Soc. Perkin Trans., 681–686 (1984).

Takano, Seiichi, et al., "A Synthesis of Trans– and Cis–Caronaldehydes", Heterocycles, vol. 23, No. 11, 2859–2872 (1985).

*Primary Examiner*—Johann Richter
*Assistant Examiner*—Ebenezer Sackey
(74) *Attorney, Agent, or Firm*—Hale and Dorr LLP

(57) ABSTRACT

A process for the preparation of cis-6,6-dimethyl-3-oxa-bicyclo[3.1.0]hexan-2-one which comprises either: 1) reacting a sulphonic ester of β,β-dimethyl-γ-(hydroxymethyl)-γ-butyrolactone with a compound of formula $M(C_{1-6}$ alkoxide$)_y$, in a suitable solvent; or 2) reacting a $C_{1-4}$ alkyl ester of 4,5-epoxy-3,3-dimethylpentanoic acid with $M(C_{1-6}$ alkoxide$)_y$, in a suitable solvent; wherein M is a suitable cation and y fulfills valency requirements.

22 Claims, No Drawings

PREPARATION OF CIS-6, 6-DIMETHYL-3-OXA-BICYCLO[3.1.0]HEXAN-2-ONE

This application is a 371 of PCT/GB99/01190 filed Apr. 19, 1999.

The present invention relates a process for making cyclopropane esters useful in the synthesis of pyrethroids which are useful as pesticides, and to intermediates useful in said process.

Esters of cis-3-(2-chloro-3,3,3-trifluoroprop-1-en-1-yl)-2,2-dimethylcyclopropane carboxylic acid with for example 3-phenoxybenzyl alcohol, α-cyano-3-phenoxybenzyl alcohol and 2-methyl-3-phenylbenzyl alcohol are important insecticidal and acaricidal products, and esters of this acid are important intermediates in the manufacture of such products. These products are all chiral and it is preferred to manufacture such products as single enantiomers or in enantiomerically enriched form.

An asymmetric synthesis of single enantiomers of 6,6-dimethyl-3-oxabicyclo[3.1.0]hexan-2-one involving a trans- to cis-isomerisation step from a hydroxyester precursor is described in *Tet. Lett.*, 1983, 24, 103. The conversion of the resulting 6,6-dimethyl-3-oxabicyclo[3.1.0]hexan-2-one to deltamethrin is also described.

The use of L-proline as a chiral auxiliary for the asymmetric synthesis of 6,6-dimethyl-3-oxabicyclo[3.1.0]hexan-2-one (I) from methyl 4,5-epoxy-3,3-dimethylpentanoate to give a mixture of cis- and trans-cyclopropyl isomers is described in *Heterocycles*, 1985, 23, 2859. This methodology does not enable the geometry of the cyclopropyl ring to be controlled. This reference also describes rearrangement of epoxyester (IIIa) to lactone (I) and trans-hydroxyester (VIa) but, under the reaction conditions, (VIa) cannot be rearranged to form (I), viz:

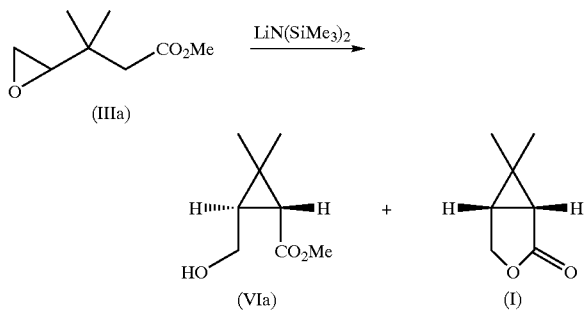

Thus, it is desirable to prepare cis-pyrethroid acids (see, for example, pyrethroid acids of formula (V) in Scheme 1) using a process under which any trans-isomer formed will be rearranged to the cis-form.

The present invention provides a process for the preparation of cis-6,6-dimethyl-3-oxa-bicyclo[3.1.0]hexan-2-one which comprises either:

a) reacting a sulphonic ester of β,β-dimethyl-γ-(hydroxymethyl)-γ-butyrolactone with a compound of formula M($C_{1-6}$ alkoxide)$_y$, in a suitable solvent; or b) reacting a $C_{1-4}$ alkyl ester of 4,5-epoxy-3,3-dimethylpentanoic acid with M($C_{1-6}$ alkoxide)$_y$, in a suitable solvent;

wherein M is a suitable cation and y fulfills valency requirements.

It is preferred that the $C_{1-6}$ alkoxide is an alkoxide that can function both as a base and a nucleophile, such as tert-butoxide.

It is preferred that M is an alkali metal salt (especially sodium or potassium), an alkaline earth metal (especially calcium or magnesium) or an organic cation (especially a quaternary ammonium such as $NH_4$ or $N(CH_3)_4$). It is especially preferred that M is sodium or potassium.

Alkyl esters of 4,5-epoxy-3,3-dimethylpentanoic acid are preferably the methyl or ethyl esters of that acid.

Sulphonic esters of β,β-dimethyl-γ-(hydroxymethyl)-γ-butyrolactone include $C_{1-4}$ alkylsulphonyl and phenylsulphonyl (wherein phenyl is optionally substituted with $C_{1-4}$ alkyl) esters, such as the mesyl and tosyl esters.

In one aspect the present invention provides a process for the preparation of cis-6,6-dimethyl-3-oxabicyclo[3.1.0]hexan-2-one which comprises either:

a) forming a sulphonic ester of β,β-dimethyl-γ-(hydroxymethyl)-γ-butyrolactone; and, b) reacting the sulphonic ester with a compound of formula M($C_{1-6}$ alkoxide)$_y$, in a suitable solvent; or reacting a $C_{1-4}$ alkyl ester of 4,5-epoxy-3,3-dimethylpentanoic acid with M($C_{1-4}$ alkoxide)$_y$, in a suitable solvent;

wherein M is a suitable cation and y fulfills valency requirements.

Sulphonic esters of β,β-dimethyl-γ-(hydroxymethyl)-γ-butyrolactone can be formed, for example, by adaptation of literature methods or by reacting an appropriate hydroxymethyl lactone with a suitable sulphonyl chloride in the presence of a suitable base or mixture of bases (such as a tri($C_{1-4}$ alkyl)amine or a di($C_{1-4}$ alkyl)aminopyridine) in a suitable solvent.

In yet another aspect the present invention provides a sulphonic ester of β,β-dimethyl-γ-(hydroxymethyl)-γ-butyrolactone.

One of the advantages of the present invention is that any entiomeric excess present in β,β-dimethyl-γ-(hydroxymethyl)-γ-butyrolactone is preserved and, thus, the process of the present invention also allows the preparation of enantiomerically enriched cis-6,6-dimethyl-3-oxabicyclo[3.1.0]hexan-2-one which, in turn, can be used to prepare enantiomerically enriched pyrethroid acids.

Thus, in another aspect the present invention provides a process for the preparation of enantiomerically enriched cis-6,6-dimethyl-3-oxabicyclo[3.1.0]hexan-2-one which comprises:

a) forming enantiomerically enriched β,β-dimethyl-γ-(hydroxymethyl)-γ-butyrolactone;

b) forming a sulphonic ester of the enantiomerically enriched β,β-dimethyl-γ-(hydroxymethyl)-γ-butyrolactone; and, c) reacting the sulphonic ester with a compound of formula M($C_{1-6}$ alkoxide)$_y$, in a suitable solvent;

wherein M is a suitable cation and y fulfills valency requirements.

In a further aspect the present invention provides a process for the preparation of enantiomerically enriched cis-6,6-dimethyl-3-oxabicyclo[3.1.0]hexan-2-one which comprises:

a) performing a Sharpless asymmetric dihydroxylation on a $C_{1-4}$ alkyl ester of 3,3-dimethyl-4-pentenoate to form enantiomerically enriched β,β-dimethyl-γ-(hydroxymethyl)-γ-butyrolactone;

b) forming a sulphonic ester of the enantiomerically enriched β,β-dimethyl-γ-(hydroxymethyl)-γ-butyrolactone; and, c) reacting the sulphonic ester with a compound of formula M($C_{1-6}$ alkoxide)$_y$, in a suitable solvent;

wherein M is a suitable cation and y fulfills valency requirements.

6,6-Dimethyl-3-oxabicyclo[3.1.0]hexan-2-one produced according to the present invention is preferably enantiomerically enriched and has an enantiomeric excess greater than 90%, preferably greater than 98%.

The term "enantiomeric excess" is defined as:

(% major enantiomer)−(% minor enantiomer)

(% major enantiomer)+(% minor enantiomer)

Enantiomerically enriched β,β-dimethyl-γ-(hydroxymethyl)-γ-butyrolactone can be prepared by Sharpless asymninetric dihydroxylation of a C$_{1-4}$ alkyl ester of 3,3-dimethyl-4-pentenoate (see, for example, H C Kolb, M S Vannieuwenhze & K B Sharpless, *Chemical Reviews,* (1994) 94(8) 2483–2547, or H Becker & K B Sharpless, *Angew. Chem. Int. Ed. Eng.* (1996) 35 448–451); or by bioresolution (see, for example S M Robert, K Wiggins & G Casy (eds.) "Preparative Biotransfornations—Whole cells and isolated enzymes in organic synthesis" John Wiley & Sons, (1993)).

In a further aspect the present invention provides a process for the preparation of a compound of formula (VI):

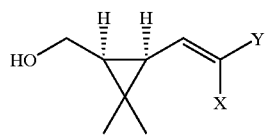

(VI)

in enantiomerically enriched form, wherein X and Y are, independently, halogen, C$_{1-3}$ alkyl or C$_{1-3}$ haloalkyl, which comprises:

a) forming enantiomerically enriched β,β-dimethyl-γ-(hydroxymethyl)-γ-butyrolactone (such as by Sharpless asymmetric dihydroxylation or bioresolution);

b) forming a sulphonic ester of the enantiomerically enriched β,β-dimethyl-γ-(hydroxymethyl)-γ-butyrolactone;

c) reacting the sulphonic ester with a compound of formula M(C$_{1-4}$ alkoxide)$_y$, in a suitable solvent to form enantiomerically enriched 6,6-dimethyl-3-oxabicyclo[3.1.0]hexan-2-one;

d) reducing the enantiomerically enriched 6,6-dimethyl-3-oxabicyclo[3.1.0]hexan-2-one under suitable conditions (such as using DIBAL in the presence of a solvent at low temperature) to provide a compound of formula (VII) in enantiomerically enriched form; and, e) ring opening said compound of formula (VII) (such as by adaptation of methodologies described in S Takano, M Tanaka, K Seo, M Hirama & K Ogasawara, *J. Org. Chem.* (1985) 50 931–936 or J Tessier *Chem Ind* (1984) 199 which describe the conversion of a lactol to a dimethylvinyl cyclopropane derivative);

wherein M is a suitable cation and y fulfills valency requirements.

Halogen includes fluorine, chlorine or bromine.

C$_{1-3}$ Alkyl and C$_{1-3}$ haloalkyl groups include methyl and trifluoromethyl.

In a still further aspect the present invention provides a process for the preparation of a compound of formula (V):

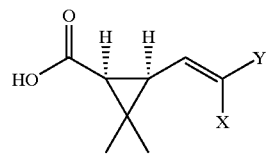

(V)

in enantiomerically enriched form, wherein X and Y are, independently, halogen, C$_{1-3}$ alkyl or C$_{1-3}$ haloalkyl, which comprises:

a) forming enantiomerically enriched β,β-dimethyl-γ-(hydroxymethyl)-γ-butyrolactone (such as by Sharpless asymmetric dihydroxylation or bioresolution);

b) forming a sulphonic ester of the enantiomerically enriched β,β-dimethyl-γ-(hydroxymethyl)-γ-butyrolactone;

c) reacting the sulphonic ester with a compound of formula M(C$_{1-6}$ alkoxide)$_y$, in a suitable solvent to form enantiomerically enriched 6,6-dimethyl-3-oxabicyclo[3.1.0]hexan-2-one;

d) reducing the enantiomerically enriched 6,6-dimethyl-3-oxabicyclo[3.1.0]hexan-2-one under suitable conditions to provide a compound of formula (VII) in enantiomerically enriched form;

e) ring opening said compound of formula (VII) to provide a compound of formula (VI) in enantiomerically enriched form; and, f) oxidising said compound of formula (VI) under suitable conditions (such as adoption or adaptation of the conditions described in G Green, W P Griffith, D M Hollinshead, S V Ley, & M Schroeder *J. Chem. Soc. Perkin Trans.* 1 (1984) 681–686; N G Bhat, B M Mane, G H Kulkarni & R B Mitra *Indian J. Chem. Sect. B* (1981) 204–206; or R S Dhillon, V K Gautam, S Singh & J Singh *Indian J. Chem. Sect. B* (1991) 574–578);

wherein M is a suitable cation and y fulfills valency requirements.

It is preferred that the process of the invention is conducted without isolating the sulphonic ester of β,β-dimethyl-γ-(hydroxymethyl)-γ-butyrolactone.

The process of the present invention, together with synthesis of the relevant starting materials, is illustrated in Scheme 1 below, wherein R is C$_{1-4}$ alkyl and R' is the residue of a sulphonic acid (such as a C$_{1-4}$ alkylsulphonic acid or a phenylsulphonic acid (wherein phenyl is optionally substituted with C$_{1-4}$ alkyl), such as methanesulphonic acid or p-toluenesulphonic acid).

Although the compounds of formulae (I), (V), (VI) and (VII) are represented in Scheme 1 in enantiomeric forms, the invention is not limited to these forms, but covers all possible enantiomeric forms of these compounds.

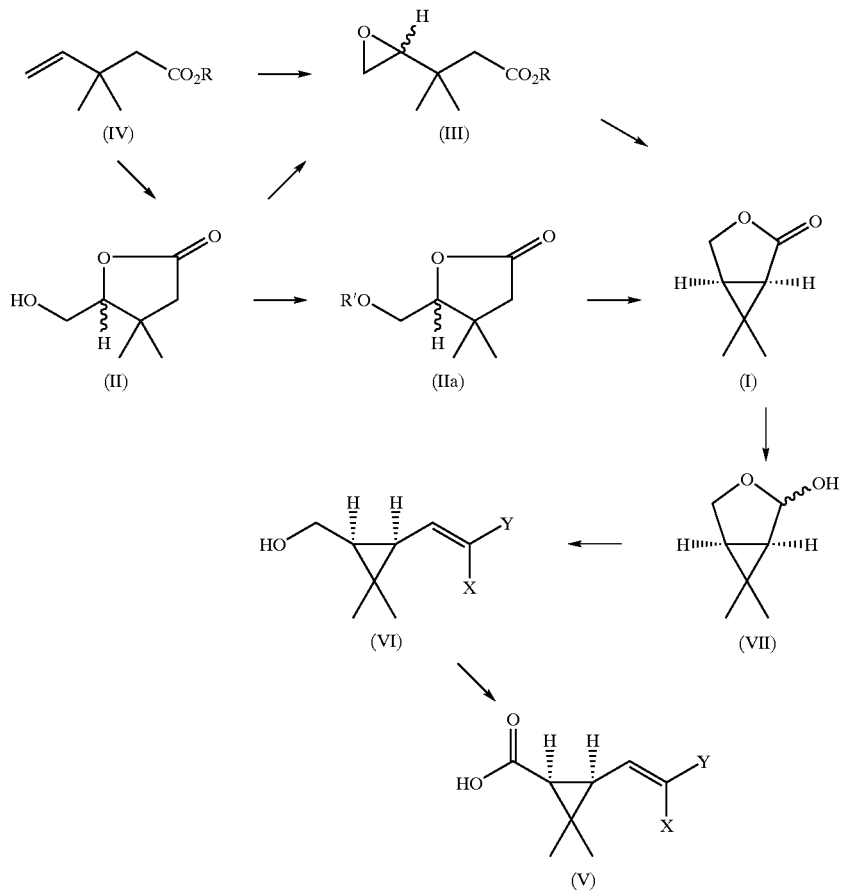

Scheme 1

As shown in Scheme 1, lactone of formula (I) may be converted into pyrethroid acids (V) via a process involving reduction to the corresponding lactol (for example using diisobutylaluminium hydride (DIBAL)) followed by opening of the resulting lactol (for example using a Wittig reaction as described in *J. Org. Chem.*, 1985, 50(7), 931–936) and finally oxidising the product so formed to the corresponding pyrethroid acid (for example as described in *Indian J. Chem. Sect. B*, 1991, 30(6), 574–578).

Examples of compounds of formula (V) include compounds having purely cis-cyclopropyl ring geometry, in racemic mixture, enantiomerically enriched or single enantiomer form, of various pyrethroid acids such as the compounds wherein: X=Y=bromine (deltamethrin acid), X=Y=methyl (chrysanthemic acid), X=chlorine and Y=methyl (permethrin acid) or X=chlorine and Y=trifluoromethyl (cyhalothrin acid).

Typically compound (I) can be made by reacting a compound of formula (IIa) or (III) with a suitable alkoxide (such as potassium tert-butoxide) in a suitable solvent (preferably an ether (such as tetrahydrofuran) or a polar solvent (such as N,N-dimethylformamide)) at an elevated temperature (such as in the range 10–100° C.).

A compound of formula (IIa) can be prepared by reacting a compound of formula (II) with a suitable sulphonic acid chloride (such as mesyl chloride or tosyl chloride) in the presence of a suitable base (such as triethylamine) in a suitable inert solvent (such as dichloromethane) preferably at ambient temperature.

A compound of formula (III) can be prepared by oxidising a compound of formula (IV) with a suitable oxidising agent (such as a peroxy acid (for example m-chloroperoxybenzoic acid)) at ambient temperature in an inert solvent (such as dichloromethane).

The invention is illustrated by, but not limited to, the following Examples.

EXAMPLE 1

This Example illustrates the preparation of racemic 6,6-dimethyl-3-oxabicyclo[3.1.0]hexan-2-one (I).

Step A, preparation of methyl 4,5-epoxy-3,3-dimethylpentanoate (III)

To a 500 ml flask was added m-chloroperoxybenzoic acid (20 g, taken as 66%) followed by dichloromethane (DCM, 235 ml). The solution was stirred and methyl 3,3-dimethyl-4-pentenoate (10 g) injected at room temperature. The reaction mixture was then left overnight. About 17 hours later the reaction was quenched with saturated $Na_2SO_3$ solution (150 ml) and the resulting mixture extracted with dichloromethane (3×50 ml). The extracts were washed with saturated $NaHCO_3$ solution, brine and dried ($MgSO_4$). The solvent was evaporated to leave the sub-titled product 10.9 g (98%). NMR showed this to be pure and therefore needed no further purification.

$^1$H NMR ($CDCl_3$): δ3.674(3H,s), 2.906(H,dd, J=2.9, 4.0 Hz), 2.707–2.621(2H,d), 2.364(1H,d), 2.275(H,d), 1.015 (3H,s), 0.995(3H,s)ppm.

Step B, preparation of 6,6-dimethyl-3-oxabicyclo[3.1.0]hexan-2-one (I)

Potassium tert-butoxide (0.43 g) was weighed into a 25 ml flask and the flask fitted with a condenser and charged with argon and tetrahydrofuran (THF, 8.5 ml). The solution was stirred and the epoxide from Step A (0.4 g) injected. The flask was then immersed in an oil bath at 75° C. After 45 minutes the flask was removed from the oil bath and left to cool for 5 minutes before quenching the reaction mixture with hydrochloric acid (5M, 5 ml). The resulting solution was extracted with diethyl ether, washed with $NaHCO_3$ solution, brine and dried ($MgSO_4$). The solvent was evaporated to leave the title compound (0.317 g, 99%). Gas chromatography and NMR showed the title product to require no further purification.

$^1$H NMR ($CDCl_3$): δ4.372(H,dd, J=9.9, 5.5 Hz), 4.155 (1H,dt, J=9.9, 1.1 Hz), 2.0515(1H,ddd, J=6.04, 5.5, 1.1 Hz), 1.953(1H,dd,J=6.04, 1.1 Hz), 1.185(3H,s), 1.176(3H,s)ppm.

EXAMPLE 2

This Example illustrates the preparation of enaniomerically enriched β,β-dimethyl-γ-(hydroxymethyl)-γ-butyrolactone (II).

A jacketed vessel was cooled to 0° C. with a circulating coolant. To the vessel was added tert-butanol (44.0 ml) followed by water (44.0 ml), $K_3Fe(CN)_6$(69.2 g), $K_2CO_3$(29 g), $OsO_4$(4.5 ml of a 4% solution in water) and (DHQD)$_2$PYR (0.62 g; see *J. Org. Chem.* 58 3785 (1993)). The resulting mixture was stirred for 10 minutes, methyl-3,3-dimethyl-4-pentenoate (10 g) added and the reaction mixture stirred for 3 days at 0° C. After quenching with saturated sodium thiosulphate solution (50 ml) the aqueous was extracted with diethyl ether. The organic extracts were combined, washed with brine, dried ($MgSO_4$) and evaporated to leave a crude product. The crude product was recrystallised from diethyl ether and petroleum ether 30/40 to give the title compound (97% yield).

$^1$H NMR ($CDCl_3$): δ4.165(H,dd, J=4.9, 4.4 Hz), 3.808 (2H,m), 2.491(H,d, J=17.0 Hz), 2.318(H,d), 1.207(3H,s), 1.127(3H,s)ppm.

EXAMPLE 3

This Example illustrates the preparation of entiomerically enriched 6,6-dimethyl-3-oxabicyclo[3.1.0]hexan-2-one (I).
Step A, preparation of methanesulfonic acid 3,3-dimethyl-5-oxo-tetrahydrofuran-2-ylmethyl ester (IIa)

To a 250 ml flask was added DCM (170 ml), 4-(N,N-dimethylamino)pyridine (DMAP, 0.4 g), and triethylamine (3.5 ml), the flask was then flushed with argon and cooled in an ice bath to 0° C. The resulting solution was stirred and mesyl chloride (2.9 ml) injected first followed by hydroxymethyl lactone (II) (prepared in Example 2; 5 g). The resulting mixture was stirred for 1 hour before quenching with $NH_4Cl$ solution (100 ml). The aqueous was extracted with DCM (3×60 ml), the extracts were combined, washed with $NaHCO_3$ solution, brine and dried ($MgSO_4$). The solvent was evaporated to leave a residue (8.8 g) which was purified by column chromatography on silica using DCM (40%), diethyl ether (40%) and petroleum ether 40/60 (20%) as eluant leaving the desired ester (7.09 g, 92%).

$^1$H NMR ($CDCl_3$): δ4.474–4.320(3H,m), 3.092(3H,s), 2.438(2H,s), 1.278(3H,s), 1.157(3H,s)ppm.
Step B, preparation of 6,6-dimethyl-3-oxabicyclo[3.1.0]hexan-2-one (I)

To a 25 ml flask was added potassium tert-butoxide (0.22 g) and dry DMF (6.7 ml). The flask was then filled with argon and a condenser fitted. The ester from Step A (0.22 g) was added with vigorous stirring and the flask immersed in an oil bath at 80° C. (Gas chromatography showed the reaction to be complete after 20 minutes with the formation of only the cis-cyclopropane.) The reaction was quenched after 20 minutes with hydrochloric acid (5M, 3 ml) and the aqueous extracted with diethyl ether. The ether extracts were combined, washed with brine, dried ($MgSO_4$) and the solvent evaporated to leave a residue (0.61 g) which was purified by chromatography on silica, using 40% diethyl ether in petroleum ether 40/60 as eluant to leave the title compound (0.11 6 g, 93% yield, enantiomeric excess 99.0%).

$^1$H NMR ($CDCl_3$): δ4.372(1H,dd, J=9.9, 5.5 Hz), 4.155 (1H,dt, J=9.9, 1.1 Hz), 2.0515(1H,ddd, J=6.04, 5.5, 1.1 Hz), 1.953(1 H,dd, J =6.04, 1.1 Hz), 1.185(3H,s), 1.176(3H,s) ppm.

Enantiomeric excess was measured under the following conditions:

Column: GPN (Gammna cyclodextrin propionyl) 10 m×0.25 mm

Injector type/temperature: Split/250° C.

Detector type/temperature: FID/250° C.

Column head pressure: 5 psi

Oven temperature: Isocratic at 130° C.

Load: 1 μg

Split: 100 ml/min

EXAMPLE 4

This Example illustrates the preparation of 6,6-dimethyl-3-oxabicyclo[3.1.0]hexan-2-ol (VII).

Dry THF (53 ml) and DIBAL solution (9.5 ml of a 1M in dichioromethane, 1.2 eq) under argon were cooled to −78° C. before injecting 6,6-dimethyl-3-oxabicyclo[3.1.0]hexan-2-one (Example 3, 1 g). The mixture was left overnight to warm to room temperature and quenched with hydrochloric acid (5M) over 5 minutes. The aqueous was extracted with diethyl ether, the ether extracts were combined, washed with saturated $NaHCO_3$ solution and brine, and then dried ($MgSO_4$). The solvent was evaporated to leave a residue which was chromatographed on silica using an eluent of diethyl ether (40%) petroleum ether 40/60 (60%) to give the title product (88%).

$^1$H NMR ($CDCl_3$): δ5.213(1H,d, J=4.4 Hz), 4.143(1H,m), 3.777(1H,d, J=8.24 Hz), 1.5225(2H,m), 1.039(3H,s), 1.033 (3H,s)ppm.

What is claimed is:

1. A process for the preparation of cis-6,6dimethy-3-oxabicyclo(3.1.0)hexan-2-one which comprises either:
    a) reacting a sulphonic ester of β,β-dimethyl-γ-(hydroxymethyl)-γ-butyrolactone with a compound of formula $M(C_{1-6}$ alkoxide$)_y$, in an ether or polar solvent; or
    b) reacting a $C_{1-4}$ alkyl ester of 4,5-epoxy-3,3-dimethylpentanoic acid with $M(C_{1-6}$ alkoxide$)_y$, in an ether or polar solvent;
wherein M is an alkali metal or quaternary ammonium cation and y is 1.
2. The process of claim 1 which comprises:
    a) reacting β,β-dimethyl-γ-(hydroxymethyl)-γ-butyrolactone with a sulphonic acid chloride to make the sulphonic ester of β,β-dimethyl-γ-(hydroxymethyl)-γ-butyrolactone.
3. The process of claim 1, wherein the $C_{1-6}$ alkoxide is tert-butoxide.

4. The process of claim 1, wherein the alkali metal is sodium or potassium.

5. A process for the preparation of cis-6,6-dimethyl-3-oxa-bicyclo (3.1.0) hexan-2one which comprises either:
 a) reacting a sulphonic ester of β,β-dimethyl-γ-(hydroxymethyl)-γ-butyrolactone with a compound of formula M($C_{1-6}$ alkoxide)$_y$, in an ether or polar solvent; or
 b) reacting a $C_{1-4}$ alkyl ester of 4,5-epoxy3,3-dimethylpentanoic acid with M($C_{1-6}$ alkoxide)$_y$, in an ether or polar solvent;
wherein M is alkaline earth metal cation and y is 2.

6. The process of claim 5 which comprises:
 a) reacting β,β-dimethyl-γ-(hydroxymethyl)-γ-butyrolactone with a sulphonic acid chloride to make the sulphonic ester of β,β-dimethyl-γ-(hydroxymethyl)-γ-butyrolactone.

7. The process of claim 5, wherein the $C_{1-6}$ is alkoxide is tert-butoxide.

8. The process of claim 5, wherein the alkaline earth metal is calcium or magnesium.

9. The process of claim 1, wherein the sulphonic ester of β,β-dimethyl-γ-(hydroxymethyl)-γ-butyrolactone is a $C_{1-4}$ akylsulphonyl ester or a phenylsulphonyl ester.

10. The process of claim 5, wherein the sulphonic ester of β,β-dimethyl-γ-(hydroxymethyl)-γ-butyrolactone is a $C_{1-4}$ alkylsulphonyl ester or a phenylsulphonyl ester.

11. The process of claim 1, wherein the ether is tetrahydrofuran.

12. The process of claim 5, wherein the ether is tetrahydrofuran.

13. The process of claim 2, wherein the sulphonic acid chloride is mesyl or tosyl chloride.

14. The process of claim 6, wherein the sulphonic acid chloride is mesyl or tosyl chloride.

15. The process of claim 1, wherein the alkali metal is $NH_4$ or $N(CH_3)_4$.

16. The process of claim 1, wherein the polar solvent is N,N-dimethylformamide.

17. The process of claim 5, wherein the polar solvent is N,N-dimethylformamide.

18. The process of claim 1, wherein the reaction is performed at a temperature in the range of 10–100° C.

19. The process of claim 5, wherein the reaction is performed at a temperature in the range of 10–100° C.

20. The process of claim 2, wherein the reaction is performed in the presence of triethylamine and dichloromethane.

21. The process of claim 6, wherein the reaction is performed in the presence of triethylamine and dichloromethane.

22. The process of claim 1, wherein M($C_{1-6}$alkoxide)$_y$ is potassium tert-butoxide.

* * * * *